US006706526B2

(12) United States Patent
Lang et al.

(10) Patent No.: US 6,706,526 B2
(45) Date of Patent: Mar. 16, 2004

(54) LOW FORMALDEHYDE PRODUCING BLOOD DILUENT

(75) Inventors: Russell F. Lang, Pembroke Pines, FL (US); Iris L. Payan, Pembroke Pines, FL (US); Barbara G. Murza, Miami, FL (US); Luisa C. Oramas, Weston, FL (US)

(73) Assignee: Coulter International Corp., Miami, FL (US)

( * ) Notice: Subject to any disclaimer, the term of this patent is extended or adjusted under 35 U.S.C. 154(b) by 72 days.

(21) Appl. No.: 10/056,617

(22) Filed: Jan. 24, 2002

(65) Prior Publication Data

US 2003/0166290 A1 Sep. 4, 2003

(51) Int. Cl.$^7$ .............................................. G01N 31/00
(52) U.S. Cl. ............................... 436/18; 436/8; 436/10; 436/66; 436/130; 436/176; 252/408.1
(58) Field of Search .................. 436/8, 10, 17, 436/18, 63, 66, 130, 176; 252/408.1

(56) References Cited

U.S. PATENT DOCUMENTS

| 4,346,018 | A |   | 8/1982  | Carter et al.          |
|-----------|---|---|---------|------------------------|
| 4,521,518 | A |   | 6/1985  | Carter et al.          |
| 4,528,274 | A |   | 7/1985  | Carter et al.          |
| 4,962,038 | A | * | 10/1990 | Carter et al. ... 436/10 |
| 4,990,525 | A |   | 2/1991  | Hsu                    |
| 5,008,202 | A | * | 4/1991  | Edmondson et al. ... 436/18 |
| 5,223,398 | A |   | 6/1993  | Kortright et al.       |
| 5,227,304 | A | * | 7/1993  | Wong ........... 436/17 |
| 5,231,005 | A |   | 7/1993  | Russell et al.         |
| 5,246,913 | A |   | 9/1993  | Hsu                    |
| 5,667,983 | A |   | 9/1997  | Abel et al.            |
| 5,733,784 | A | * | 3/1998  | Studholme et al. ...... 436/63 |
| 5,786,224 | A | * | 7/1998  | Li et al. .............. 436/63 |
| 5,888,752 | A |   | 3/1999  | Malin et al.           |
| 5,935,857 | A |   | 8/1999  | Riesgo et al.          |
| 6,225,124 | B1|   | 5/2001  | Houwen et al.          |
| 6,468,732 | B1| * | 10/2002 | Malin et al. ........... 435/2 |
| 6,524,858 | B1| * | 2/2003  | Zelmanovic et al. ..... 436/10 |
| 2002/0098589 | A1 | * | 7/2002 | Crews et al. ........ 436/10 |

FOREIGN PATENT DOCUMENTS

EP        0 872 734 B1     3/2001

OTHER PUBLICATIONS

Good, N.E., et al., *Biochemistry*, vol. 5, No. 2, 467–477 (1966).
Good, N.E., et al., "Photosynthesis and Nitrogen Fixation", *Methods in Enzymology.*, vol. XXIV, 53 (1972).

* cited by examiner

*Primary Examiner*—Maureen M. Wallenhorst
(74) *Attorney, Agent, or Firm*—Howson and Howson; Mitchell E. Alter

(57) ABSTRACT

A low formaldehyde containing aqueous blood diluent contains an effective amount of ethylenediamine tetraacetic acid, ethylenediamine tetraacetic acid derivative, or combinations thereof; an effective amount of 5-chloro-2-methyl-4-isothiazolin-3-one and 2-methyl-4-isothiazolin-3-one; and an effective amount of 5-bromo-5-nitro-1,3-dioxane. Advantageously, less than about 1 parts per million of formaldehyde is produced in this multipurpose diluent. A method of analyzing a blood sample containing blood cells is conducted by forming a diluted blood sample by mixing a blood sample containing blood cells with this diluent and analyzing the diluted blood sample to determine a physical parameter of the blood cells.

25 Claims, No Drawings

LOW FORMALDEHYDE PRODUCING BLOOD DILUENT

BACKGROUND OF THE INVENTION

This invention relates to the fields of hematology and immunology and to reagents used for analyzing blood cells. More specifically, the present invention relates to an improved diluent which produces less than about 1 part per million of formaldehyde during both usage and storage.

Common medical diagnostic procedures involve the analysis of a blood sample of a patient in order to make certain clinical diagnoses. For example, complete blood counts, analyses of the white and red cell numbers and/or subpopulations, and the presence of unusual cell types as detected by a variety of flow cytometric assays provide valuable information for the physician. Regardless of the subsequent steps to be performed in any of the well-known diagnostic analytic procedures for blood samples, the first step is generally a dilution of the blood sample. Specifically, the blood sample is diluted with a diluent that may contain a mixture of salts, buffers, and preservatives, among others. See, e.g., the discussion of the contents and problems of prior art diluents in U.S. Pat. No. 5,935,857, for example.

However, the use of many commercially available blood diluents has been restricted due to the regulation of institutional and industrial, including medical, wastes. For example, regulatory agencies in the states of California and Massachusetts, for example, are increasingly requiring reduced concentrations of formaldehyde in wastewater. Unfortunately, at present, most of the commercially available blood diluents produce formaldehyde in amounts in excess of about 400 parts per million, or if there is an absence of formaldehyde producing components, the diluent contains other undesirable components, such as sodium azide, or does not have the broad biocidal protection.

There exists a need in the art for a multipurpose blood diluent which produces considerably less than about 400 parts per million of formaldehyde and does not negatively impact the analysis of samples, has broad biocidal activity and does not contain undesirable components.

SUMMARY OF THE INVENTION

The present invention is directed toward blood diluents which produce less than about 1 part per million of formaldehyde. The present invention is also directed toward such substantially formaldehyde-free diluents, which maintain good antimicrobial activity, but do not adversely affect essential parameters of blood analysis, such as mean corpuscular volume (MCV) and other blood cell parameters.

The present invention is further directed toward methods of analyzing a blood sample containing blood cells using the blood diluents of the invention.

These and other aspects of the invention will be understood to one of skill in the art upon reading of the following detailed description of the invention.

DETAILED DESCRIPTION OF THE INVENTION

The present invention resolves the problem of formaldehyde production by blood diluents by providing a novel blood diluent which contains less than about 1 part per million of formaldehyde. Further, methods for analyzing the blood samples to determine at least one physical parameter of the blood sample using the blood diluents of the invention are provided.

I. The Diluent Composition

The present invention provides a low formaldehyde-containing aqueous blood diluent containing a first component selected from specified potentiator reagents and a second component which is a combination of an effective anti-microbial amount of 5-chloro-2-methyl-4-isothiazolin-3-one, 2-methyl-4-isothiazolin-3-one; and 5-bromo-5-nitro-1,3-dioxane. The compositions are combined in concentrations and with other components that permit less than about 1 parts per million of formaldehyde to be produced in the diluent.

The phrase "low formaldehyde" as used herein and throughout this specification is meant to describe a solution having or producing less than about 1 part per million (ppm) of formaldehyde over a period of time of at least 1 year. In one embodiment, "low formaldehyde" describes a solution having or producing less than about 0.70 ppm of formaldehyde. In another embodiment, "low formaldehyde" describes a solution having or producing less than about 0.60 ppm of formaldehyde. In a further embodiment, "low formaldehyde" describes a solution having or producing less than about 0.50 ppm of formaldehyde. In yet another embodiment, "low formaldehyde" describes a solution having or producing less than about 0.40 ppm of formaldehyde. In another embodiment, "low of formaldehyde" describes a solution having or producing less than about 0.30 ppm of formaldehyde. In yet a further embodiment, "low formaldehyde" describes a solution having or producing less than about 0.20 ppm of formaldehyde. In another embodiment, "low formaldehyde" describes a solution having or producing less than about 0.10 ppm of formaldehyde.

The inventors have recently discovered that preservative agents contribute significantly to the production of formaldehyde in commercially available blood diluents. Specifically, the widely used preservative agent dimethylolurea (DMOU) has been found to produce greater than 1 part per million of formaldehyde both alone and in combination with other reagents. Since the blood diluents of the invention produce less than about 1 ppm formaldehyde, it is preferable for reagents that produce or contain greater than 1 ppm of formaldehyde to be omitted from the composition of the diluent of the invention. Since the inventors have discovered that dimethylolurea produces greater than 1 ppm formaldehyde, it is preferably completely excluded from the diluent composition of the invention.

As used herein and throughout this specification, an "effective amount" of a component is selected with regard to the pH, osmolality, concentration, conductivity and/or antimicrobial efficacy of the final diluent composition and with respect to the function of the particular component. One of skill in the art would readily be able to determine the effective amount of each component. While specific ranges are noted, alternate amounts may also be contemplated by one of skill in the art.

The term "aqueous" as used herein and throughout this specification is meant to describe a solution having water as its main component. The solution may additionally contain other chemical compounds and/or solvents that do not interfere with the effectiveness of the diluent. Such additional solvents may be selected by one of skill in the art and include, but are not limited to, organic solvents, inorganic solvents, and saline solutions.

A. Potentiator Reagents

As described herein, the present invention is directed toward a low formaldehyde-containing aqueous blood diluent that contains one or more potentiators as a first component. Without wishing to be bound by theory, the blood diluent potentiator is a compound that chelates ions in the cell membrane and weakens the membrane, making the cell more susceptible to biocides. In one embodiment, one potentiator may be ethylenediamine tetraacetic acid (EDTA), an EDTA derivative, or combinations thereof. In another embodiment, the potentiator is an EDTA derivative. For example, in an embodiment, the potentiator is disodium EDTA. In another embodiment, the potentiator is dipotassium EDTA. In still another embodiment, the potentiator is ethyleneglycol-bis-(2-aminoethyl ether)N,N,N',N'-tetraacetic acid (EGTA). More preferably, the potentiator is disodium EDTA.

In another embodiment, additional potentiators other than EDTA or its derivatives may be added to the diluent. Such additional potentiators include potentiators that chelate ions as described above, which are known to those skilled in the art. Some of these potentiators include, without limitation, cyclohexanediamine-tetraacetic acid, diethylentriaminepentaacetic acid, and/or hydroxyethylethylene-diaminetriacetic acid. Still other potentiators which function via mechanisms other than chelation are known and may also be mixed with a chelating potentiator into the biocidal formulation of the diluent.

The concentration of each potentiator in the diluent is typically present from about 0.05 grams per liter (g/L) to about 2.0 g/L. Preferably, the concentration of the potentiator is from about 0.05 to about 1.5 g/L.

The term "derivative" as used herein and throughout this specification is meant to describe a compound that is structurally similar to the parent compound. Derivatives may include, but are not limited to, salts that may be derived from pharmaceutically or physiologically acceptable inorganic or organic acids and bases, and organically acceptable variations thereof.

B. Antimicrobial Agents

Diagnostic reagents may be stored for extended periods while during use and manufacture, and can often be exposed to microorganisms. Thus, the diluent of this invention must exhibit antimicrobial robustness, since the presence of such microorganisms contaminating the diluent can distort the analysis of the sample. Antimicrobial agents must be utilized to eliminate growth of microorganisms prior to and during analysis. The term "antimicrobial agent" as used herein and throughout this specification is meant to describe any chemical compound that is effective in reducing or eliminating microorganisms including, but not limited to, gram positive bacteria, gram negative bacteria, fungi, and yeast. However, as noted above, antimicrobial agents used in the diluents known in the art have been found by the inventors to at least contribute to the production of greater than 1 ppm of formaldehyde in the diluent. For use in the diluent of this invention, antimicrobial agents must have the following characteristics: In association with other components of the diluent composition, these reagents must produce little or insubstantial amounts (e.g., preferably, less than 1 ppm) of formaldehyde. The reagents must also provide adequate antimicrobial protection and yet not interfere with the measurement of the blood sample in the various analytical procedures. Preferably, the antimicrobial agents do not react with lytic, or other, reagents conventionally used in many methods of blood analysis.

The blood diluent of the invention thus contains one or more antimicrobial agents which are effective in eliminating gram negative bacteria, gram positive bacteria, yeast, and fungi, and yet which produce in the diluent composition less than 1 ppm formaldehyde. Preferably, the antimicrobial agents useful in the diluent of the invention include various combinations of 5-chloro-2-methyl-4-isothiazolin-2-one, 2-methyl-4-isothiazolin-3-one, and 5-bromo-5-nitro-1,3-dioxane and derivatives of each of these compounds.

These antimicrobial agents are commercially available. The 5-chloro-2-methyl-4-methyl-4-isothiazolin-2-one and 2-methyl-4-isothiazolin-3-one are supplied in combination commercially by Supelco, under the trademark Proclin. For example, aqueous combinations of these antimicrobial agents include the Proclin® 150 reagent (Supelco), which is an aqueous mixture of 1.15% of 5-chloro-2-methyl-4-isothiazolin-3-one and 0.35% of 2-methyl-4-isothiazolin-3-one, and the Proclin® 300 reagent (Supelco), which is a mixture of 2.3% of 5-chloro-2-methyl-4-isothiazolin-3-one and 0.7% of 2-methyl-4-isothiazolin-3-one in a solvent consisting of a modified glycol and alkyl carboxylate. Another product supplied commercially by the same company is called Proclin® 5000 reagent, which contains only 2-methyl-4-isothiazolin-3-one in a dipropylene glycol solvent. The biocide 5-bromo-5-nitro-1,3-dioxane is commercially available and include the Bronidox® L reagent (Cognis Corporation).

When added as neat reagents, neat 5-chloro-2-methyl-4-isothiazolin-2-one and neat 2-methyl-4-isothiazolin-3-one are present in the diluent at a combined concentration of about 0.0015 to about 0.030 g/L at a ratio of about 1: about 0.3 (5-chloro-2-methyl-4-isothiazolin-2-one: 2-methyl-4-isothiazolin-3-one). As used herein and throughout this specification, the term "neat" is meant to describe a reagent alone, without additional solvents or reagents. The fixed ratio of the two components as provided in the commercial Proclin® reagents have been shown to be acceptable for use in the diluent of this invention. However, other ratios of these two components may also be determined by one of skill in the art. Additionally, useful individual concentrations of the two components may be calculated readily from these preparations. More preferably, neat 5-chloro-2-methyl-4-isothiazolin-2-one and neat 2-methyl-4-isothiazolin-3-one may be added to the diluent of the invention and are present in the diluent at a combined concentration of about 0.005 to about 0.01 g/L. In another embodiment, 5-chloro-2-methyl-4-isothiazolin-2-one and neat 2-methyl-4-isothiazolin-3-one may be added to the diluent of the invention as mixtures that are commercially available. When antimicrobial agents are added as a mixture, the Proclin® 150 reagent may preferably be present in the diluent at a concentration of about 0.1 to about 2.0 $\mu$L. More preferably, the Proclin® 150 reagent may be present in the diluent at a concentration of about 0.25 to about 1.0 $\mu$L. The present invention is however not bound by the specific source of these antimicrobial agents or concentrations of the Proclin® reagents.

The other antimicrobial agent, 5-bromo-5-nitro-1,3-dioxane functions in the diluent to assist in eliminating gram-positive bacteria and provide other broad biocidal activity against other organisms and does not produce or contain greater than 1 ppm of formaldehyde when employed in the blood diluent of the invention. In one embodiment, neat 5-bromo-5-nitro-1,3-dioxane is employed in the diluent at a concentration of about 0.010 to about 0.50 g/L and preferably from about 0.015 to about 0.30 g/L. In another embodiment, the Bronidox® L reagent is employed as the source of 5-bromo-5-nitro-1,3-dioxane and is present in the diluent at a concentration of about 0.1 to about 2.0 g/L. More preferably, the Bronidox® L reagent may be present in the diluent at a concentration of about 0.5 to about 1.5 g/L.

When employed in combination in the diluent formulation of this invention, these three anti-microbial compounds may be employed in any ratio effective to combat microbial growth, without producing formaldehyde, and further without adversely effecting the blood sample or blood cell parameter to be measured by the selected analytical procedures. Preferably, the ratio is that of the fixed ratio of the Proclin® 150 product with the above-indicated amounts of the Bronidox® L reagent. Useful individual ratios of the three components may be calculated readily from these preparations. However, other ratios of these three components may also be determined by one of skill in the art.

Given the requirements of for multipurpose blood diluents set out by the present inventors in the instant specification, it is anticipated that other antimicrobials may be similarly useful in diluent compositions of this invention. Selection of such useful antimicrobial components following the teachings contained herein is encompassed by this invention.

C. Other Diluent Components

The diluent of the present invention may also contain other components that produce less than 1 ppm formaldehyde in combination with the first three components. Preferably these other components produce little or no formaldehyde in combination with reagents commonly used in blood sample analysis, e.g., lytic reagents, and do not interfere with the analysis of the blood samples.

In one embodiment, the diluent may contain as an added component, an alkali metal sulfate. Without wishing to be bound by theory, the alkali metal sulfate regulates the osmolality and ionic strength of the diluent. Preferably, the alkali metal sulfate includes, but is not limited to, sodium and potassium sulfates. More preferably, the alkali metal sulfate is sodium sulfate. In one embodiment, the alkali metal sulfate is added to the diluent as an aqueous solution. In another embodiment, the alkali metal sulfate is added to the diluent as a solid. Preferably, the alkali metal sulfate is present in the diluent at a concentration of about 7 to about 14 g/L. More preferably, the alkali metal sulfate is present in the diluent at a concentration of about 8 to about 12 g/L.

The diluent may also contain as an additional component, an alkali metal chloride. Without wishing to be bound by theory, the alkali metal chloride assists the alkali metal sulfate in regulating the osmolality and ionic strength of the diluent. Preferably, the alkali metal chloride includes, but is not limited to, sodium and potassium chlorides. More preferably, the alkali metal is sodium chloride. In one embodiment, the alkali metal chloride is added to the diluent as an aqueous solution. In another embodiment, the alkali metal chloride may be added to the diluent as a solid. Preferably, the alkali metal chloride is present at a concentration of about 2 to about 6 g/L. More preferably, the alkali metal chloride is present at a concentration of about 3 to about 5 g/L.

The diluent may additionally contain a base. Without wishing to be bound by theory, the base is added to the diluent in an amount sufficient to adjust the pH of the diluent to the preferred range. Adjustment of the amount of the base to provide a suitable pH is based upon the buffer employed and is within the skill of the art. Preferably, the base is an alkali metal hydroxide, however other bases may be utilized provided that they do not interfere with the analysis of the blood sample and may be selected by one of skill in the art. More preferably, the alkali metal hydroxide includes sodium and potassium hydroxide. Most preferably, the alkali metal hydroxide is sodium hydroxide. In one embodiment, the base is added as an aqueous solution. In another embodiment, the base is added as an aqueous 50% sodium hydroxide solution. In a further embodiment, the base is added to the diluent as a solid.

The desired pH of the diluent depends upon the hematology instrument utilized and the test to be performed. Preferably, the diluent will be adjusted such that the pH of the diluent is from about 5 to about 8. More preferably, the diluent will be adjusted such that the pH of the diluent is from about 6 to about 7.5. Even more preferably, the diluent will be adjusted such that the pH of the diluent is from about 6.5 to about 7.6. Sodium hydroxide base is present in the diluent at a concentration sufficient enough to achieve the desired pH. This concentration is dependent on the concentration of other solutes that may contribute to the overall acidity or basicity of the diluent solution. One of skill in the art may readily determine the amount of base required.

The diluent may also contain as a desirable component, a cell stabilizing agent that prevents platelet aggregation. An exemplary cell stabilizing agent is an anesthetic. Preferably, the anesthetic is ethyl p-aminobenzoate hydrochloride. However, other anesthetics or cell stabilizing agents may be selected and utilized in the diluent by one of skill in the art following the teachings of this invention. In one embodiment, neat ethyl p-aminobenzoate hydrochloride is added to the diluent. In another embodiment, the Procaine® hydrochloride reagent (Aceto Corp.) may be added as the source of ethyl p-aminobenzoate hydrochloride. Preferably, ethyl p-aminobenzoate hydrochloride is present in the diluent at a concentration of about 0.05 to about 0.25 g/L. More preferably, ethyl p-aminobenzoate hydrochloride is present in the diluent at a concentration of about 0.07 to about 0.15 g/L.

Additionally, the diluent may contain a buffer. Without wishing to be bound by theory, the buffer primarily maintains the pH of the diluent. In one embodiment, the buffer is N-(2-acetoamido)iminodiacetic acid (ADA). This buffer has also been reported to assist in lysing erythrocyte debris, and stabilizing the size distribution and cellular shape of erythrocytes and platelets. However, other buffers such as the Good buffers identified in Good, N. E. et al. (1966) Biochemistry 5, 467 and Good, N. E., and Izawa, S. (1972) *Methods Enzymol.* 24, 53 may be utilized depending upon the functional requirements of the formulation as determined by one skilled in the art. Preferably, N-(2-acetoamido) iminodiacetic acid is present in the diluent at a concentration of about 1.0 to about 2.5 g/L. More preferably, N-(2-acetoamido)iminodiacetic acid is present in the diluent at a concentration of about 1.2 to about 2.0 g/L.

The diluent may further contain other reagents including preservative agents, anticoagulants, detergents, dyes, and stains. See, for example, U.S. Pat. Nos. 5,935,857 and 4,528,274. However, any additional compounds added to the diluent must not increase the formaldehyde production nor adversely impact the physical parameters that are analyzed.

In one preferred embodiment, a diluent of this invention contains disodium ethylenediamine tetraacetic acid, 5-chloro-2-methyl-4-isothiazolin-3-one and 2-methyl-4-isothiazolin-3-one, 5-bromo-5-nitro-1,3-dioxane, sodium chloride, sodium sulfate, sodium hydroxide, ethyl p-aminobenzoate hydrochloride, and N-(2-acetoamido) iminodiacetic acid in suitable amounts to produce less than about 1 part per million of formaldehyde, to perform suitably as an antimicrobial, and to perform suitably as a blood diluent or sheath fluid.

Still another particularly desirable diluent composition according to this invention is illustrated in Table 1, below:

TABLE 1

| Component | General Concentration (g/L) | Preferred Concentration (g/L) |
| --- | --- | --- |
| EDTA, EDTA derivative, or combinations thereof | 0.05 to 5.0 | 0.1 to 3.0 |
| 5-chloro-2-methyl-4-isothiazolin-3-one and 2-methyl-4-isothiazolin-3-one | 0.0015 to 0.030 | 0.005 to 0.01 |
| 5-bromo-5-nitro-1,3-dioxane | 0.01 to 0.5 | 0.015 to 0.30 |
| alkali metal chloride; | 2 to 6 | 3 to 5 |
| alkali metal sulfate; | 7 to 14 | 8 to 12 |
| alkali metal hydroxide; | variable* | Variable |
| ethyl p-aminobenzoate hydrochloride | 0.05 to 0.25 | 0.07 to 0.15 |
| N-(2-acetoamido)imino-diacetic acid | 1.0 to 2.5 | 1.2 to 2.0 |
| Water | Up to 1 liter | Up to 1 liter |

*The term variable is meant describe a concentration and amount which varies in each composition, but is readily determined by one of skill in the art.

The diluent composition as described in Table 1 produces less than about 1 part per million of formaldehyde, to perform suitably as an antimicrobial, and to perform suitably as a blood diluent or sheath fluid.

These and other diluents of the present invention do not degrade during the shelf life of the product. The shelf life of the product takes into account the time from manufacture of the product through the time of customer usage of the product. Preferably, the diluent has a shelf life greater than 1 month. More preferably, the diluent has a shelf life greater than 3 months. Most preferably, the diluent has a shelf life greater than 12 months. Based on additional recent data, it is anticipated that the diluent has a shelf life of 18 months or more.

The diluents according to this invention may also be used over a wide range of operating temperatures. The diluent may be frozen and, once thawed and thoroughly mixed, performs satisfactorily. The diluent has been heated to about 150° F. for up to 36 days with no deterioration of performance. The diluent is typically used over a temperature range from about 60° F. to about 90° F. consistent with the allowable operating temperature range of Coulter hematology instruments.

Generally, the diluent will be iso-osmotic. Preferably, the osmolality is from about 250 to about 350 milliOsmo/kg (mOsm/kg). More preferably, the osmolality will be from about 300 to about 340 mOsm/kg. However, the osmolality of the diluent can vary when used it is with a lytic reagent composition. The volume of the diluent can however be adjusted relative to a lytic reagent volume to effect an optimum final osmolality of the blood sample mixture.

In addition, when used as a sheath fluid in flow cytometry analysis, the relationship between the osmolality and conductivity of the sheath fluid and the osmolality and conductivity of the core fluid should be maintained. For example, the diluent will typically have a conductivity from about 16 to 22 mS/cm.

Still another advantage of the low formaldehyde diluents of this invention is that analytic parameters of the blood sample diluted with a diluent of this invention are comparable to measurements obtained when using a commercially available diluent. For example, the diluents of the present invention provide stable MCV for fresh and aged blood as demonstrated in the examples below. Other parameters of blood analysis should remain undistorted by use of this diluent composition.

II. Methods of Using the Blood Diluent Composition

The multipurpose blood diluent of the present invention is useful in a variety of known analytic methods performed on a diluted blood sample to determine at least one physical parameter of the blood sample. In addition, the diluent of the present invention is useful as a sheath fluid for the analysis of blood samples in a focus flow instrument. More particularly, the diluent of the present invention has background fluorescence suitable for use in a fluorescence measurement of a body fluid. Suitable blood samples may be obtained from a veterinary or human patient and include, but are not limited to, whole blood, plasma, serum and urine.

Blood samples may be fresh, i.e. tested within about 8 hours from phlebotomy, or the samples may be aged for longer periods of time up to 72 hours either at room temperature or refrigerated. Preferably, aged blood samples may be analyzed within 48 hours either at room temperature or refrigerated. Most preferably, aged blood samples may be analyzed within 24 hours either at room temperature or refrigerated.

For example, the diluent is useful in methods for the determination of hematologic parameters of the blood samples. Such parameters include one or more of cell size, shape, content and volume and may include white blood cell count (WBC), red blood cell count (RBC), hemoglobin (HGB), hematocrit (HCT), mean corpuscular volume (MCV), mean corpuscular hemoglobin (MCH), mean corpuscular hemoglobin concentration (MCHC), platelet count (PLT), Plateletcrit (PCT), mean platelet volume (MPV), platelet distribution width (PDW), neutrophils (NE), lymphocytes (LY) monocytes (MO), eosinophils (EO), basophils (BA), and reticulocytes (RET).

Such measurements may be made using light scatter, low frequency current, radio frequency current, fluorescence and combinations thereof. The diluent is also conveniently used as a sheath fluid in focused flow cytometry for differentiating white blood cells into three or more subpopulations, or for determination of five subpopulations of leukocytes, and for fluorescence flow cytometry analysis when using fluorescence probes or antibodies. For example, U.S. Pat. Nos. 5,223,398 and 5,231,005 describe various methods for producing a five-part differential of white blood cells into lymphocyte, monocyte, neutrophil, eosinophil, and basophil classes. This five-part differential is accomplished in automated equipment that detects differences in cell volume (V), cell conductivity (C), and light scatter (S). One of skill in the art can readily select other methods for analysis of blood samples that can make use of the diluent compositions of this invention. It is understood that the advantages of the diluent compositions of this invention make it a desirable component of many such analytic procedures, both automated or non-automated.

The following examples are provided to illustrate the production and activity of representative compounds of the invention and to illustrate their performance in a screening assay. One skilled in the art will appreciate that although specific reagents and conditions are outlined in the following examples, these reagents and conditions are not a limitation on the present invention.

EXAMPLES

Example 1

Comparison of a Variety of Blood Diluent Compositions

This example illustrates the presence and/or production of formaldehyde in a variety of test blood diluent compositions containing different commercially available antimicrobial reagents, which are identified by their respective trademarks in Table 2 below. Diluent components into which the listed antimicrobials were added were:

| | |
|---|---|
| EDTA | 0.1 to 3.0 g/L |
| sodium chloride | 3 to 5 g/L |
| sodium sulfate | 8 to 12 g/L |
| sodium hydroxide 50% | sufficient for pH 6.0 to 7.5 |
| ADA | 1.2 to 2.0 g/L |
| ethyl p-aminobenzoate hydrochloride | .07 to 0.15 g/L |

Each test diluent was assayed for formaldehyde production within about two weeks from time of production to determine if formaldehyde is produced. Different lots of the final diluent formulation were monitored for formaldehyde concentration over a year's time. Formaldehyde was measured using EPA Method 8315A. This method entails derivitizing the diluent sample with 2,4-dinitrophenylhydrazine to convert the carbonyl groups of aldehydes present to the hydrazones. Each carbonyl compound present in the sample forms a separate hydrazone derivative and these individual derivatives are extracted from the diluent solution using an organic solvent. The individual hydrazone derivatives are separated and quantified by HPLC (High Performance Liquid Chromatography).

The results of this assay are reported in Table 2 by listing the trademark of each antimicrobial agent, the concentration of the antimicrobial agent in the diluent, the ability to produce less than 1 ppm formaldehyde at the time of measurement, and additional data on characteristics of the diluent containing the specified antimicrobial agent. Note that prior to this invention, the propensity of these antimicrobial compounds to produce formaldehyde in a diluent was uncertain.

TABLE 2

| AntiMicrobial Agent by Trademark | Concentration (g/L) | <1 ppm Formaldehyde | Additional Data |
|---|---|---|---|
| Proclin ® 150 | 0.05–0.1 | Yes | — |
| Proclin ® 300 | 0.02–0.07 | Yes | — |
| Germall ® II | 0.1–0.3 | No | — |
| Germall ® Plus | 0.05–0.02 | No | — |
| Dantoguard ® Plus | 0.03–0.30 | No | — |
| Glydant ® | About 0.4 | No | — |
| Dantoguard ® | About 0.4 | No | — |
| Bronidox ® L | 0.25 | Yes | — |
| Dowicil ® 200 | 0.02–0.3 | No | — |
| Integra ® 44 | 0.2–1.0 | Not evaluated | Destroys RBCs. Not useable. |
| Bronopol ® | <0.1 | No | — |
| Myacide ® SP | 0.05 | Yes | Low solubility and Precipitated in solution |
| LiquiPar ® | 0.5 | Yes | Low solubility and Precipitated in solution |
| IPBC ® | 0.01 | Yes | Low solubility and Precipitated in solution |

These data indicate that test diluents containing only the Proclin(150 reagent, Proclin® 300 reagent, and Bronidox® L reagent produce less than 1 ppm of formaldehyde. Such diluents do not have other negative characteristics, for example, problems with solubility or precipitation, which would adversely affect the analysis of the blood samples in known analytic methods, including flow cytometric analyses.

Example 2

Production of Formaldehyde in Stored Blood Diluent Compositions of the Invention This example illustrates the stability of the low production of formaldehyde in the blood diluent compositions of the instant invention.

Three diluent samples were prepared using the components illustrated in Table 1 above. Samples 1, 2 and 3 and 4 are different "lots" of the diluent used to confirm the performance, and to determine any deficiencies in the robustness of the new formula. These different lots of diluent were characterized by different volume sizes; using different lots of as many of the raw materials as possible; different storage container sizes; and tested on different hematology instruments. The samples were then stored at the temperatures and periods of time as noted in Table 3 below. The samples were then removed and the formaldehyde concentrations were determined by EPA Method 8315A, as described in Example 1.

TABLE 3

| Sample | Storage Temperature | Days From Manufacture | Formaldehyde Concentration (ppm) |
|---|---|---|---|
| 1 | RT | 13 | 0.095 |
|   | RT | 91 | 0.51 |
|   | RT | 154 | 0.52 |
| 2 | RT | 49 | 0.39 |
|   | RT | 112 | 0.50 |
|   | 30° C. | 30 | 0.64 |
| 3 | RT | 36 | 0.20 |
|   | RT | 170 | 0.36 |
| 4 | RT | 6 | 0.076 |
|   | RT | 30 | 0.149 |
|   | RT | 60 | 0.277 |
|   | RT | 137 | 0.437 |
|   | RT | 287 | 0.89 |
|   | RT | 386 | 0.84 |

* RT denotes room temperature

As illustrated in Table 3, less than 1 part per million of formaldehyde is produced in the blood diluent compositions of the invention over a storage time of up to 386 days, thereby illustrating that the diluent compositions of this invention stably produce less than 1 ppm formaldehyde over expected storage times.

Example 3

Antimicrobial Effectiveness and MCV Comparison of Blood Diluents

This example illustrates the antimicrobial effectiveness of the blood diluent of the invention, as well as other test diluents in blood samples. This example further compares the effect of the diluent of this invention on a blood sample parameter, e.g., the measurement of MCV, with that of a known, commercially available Isoton® III diluent (Coulter Corp.), which formulation is described in U.S. Pat. Nos. 4,346,018; 4,521,518; and 4,528,274, incorporated herein by reference.

The test diluent compositions were prepared utilizing the following components listed in Table 4 below including indicated ranges for EDTA, EDTA derivative, or combinations thereof, and the anti-microbial components. The 5-chloro-2-methyl-4-isothiazolin-3-one and 2-methyl-4-isothiazolin-3-one were supplied in the commercially available formation of Proclin® 150 or 300 reagents. The 5-bromo-5-nitro-1,3-dioxane was supplied in the commercially available formulation of Bronidox® L reagent.

The formula of Isoton III® diluent, which contains DMOU, was as provided commercially (Coulter Corp.). See also the US patents cited above.

The test diluent samples were prepared by combining varying amounts of the antimicrobial compositions listed in Table 4. The test diluent formulations used varying formulations of the diluent of this invention. Each test diluent differed from each other test diluent only by the amount of the anti-microbial reagents. The test diluent used in formulations #1 and #3 contained no 5-chloro-2-methyl-4-isothiazolin-3-one and 2-methyl-4-isothiazolin-3-one anti-microbial reagents and therefore do not represent use of a test diluent of this invention. These samples were then assayed for mean cell volume and anti-microbial effectiveness of the diluents in the blood samples as follows.

A. MCV Measurements

The MCV of each test sample was measured using a variety of COULTER® hematology analyzers, examples being GEN•S™, STKS™, MAXM™ and HMx™ instruments, according to manufacturer's instructions. The MCV typically increases as the blood sample ages due to a weakening of the cell membrane. This increase in MCV is sample dependent but typically is about 2 fL for Isoton® III diluent, which is used as a reference value. The δ MCV is defined as the difference between the MCV of aged blood minus the MCV of fresh blood. The δ MCV results utilizing the test diluents compared to the δ MCV results utilizing Isoton® III diluent are shown in Table 4. It is preferable for the δ MCV values using the diluent formulation of this invention to be similar to those of the Isoton® III diluent.

TABLE 4

| Test | Proclin® 150 reagent (g/L) | Bronidox® L reagent (g/L) | Na₂EDTA (g/L) | Proclin® 300 reagent (g/L) | δ MCV[1] for Samples diluted with |       |
|------|-----|-------|-----|-----|-------|-------|
|      |     |       |     |     | Isoton® III Diluent | Test Diluents |
| 1    | 0   | 0.025 | 0   | 0   | 1.55[2] | 1.80[2] |
| 2    | 0.5 | 0.025 | 0.1 | 0   | 1.28 | 1.18 |
| 3    | 0   | 0.025 | 0.1 | 0.5 | 1.28 | 1.48 |
| 4    | 0.5 | 1     | 0.1 | 0   | 2.01 | 1.29 |
| 5    | 0.5 | 1     | 1   | 0   | —    | —    |
| 6    | 0.5 | 1     | 0.1 | 0   | 2.64 | 2.31 |
| 7    | 0.5 | 1     | 1   | 0   | 2.64 | 2.17 |
| 8    | 0.5 | 1     | 1   | 0   | 2.16 | 2.13 |
| 9    | 0.5 | 0.5   | 1   | 0   | 2.16 | 2.30 |
| 10   | 0.5 | 0.25  | 1   | 0   | —    | —    |
| 11   | 0.5 | 1     | 1   | 0   | 1.45 | 1.91 |
| 12   | 0.5 | 1     | 1   | 0   | 1.12 | 1.81 |

[1] δ MCV: MCV of aged blood sample - MCV of fresh blood sample
[2] MCV for fresh blood using test diluent was 2.32 fL less than MCV of fresh blood using Isoton® III diluent.

The results of MCV measurements illustrate that the MCV of aged blood obtained using the test diluents containing the biocide combinations of this invention are comparable with MCV results of aged blood obtained using the known performance standard, Isoton® III diluent, which produces desirable results in these analyses but does produce formaldehyde.

B. Antimicrobial Effectiveness

The antimicrobial effectiveness of each test diluent formulation #1-12 described above was determined by monitoring the effect of each test diluent composition on the viability of at least thirteen exemplary microorganisms. The thirteen different microorganisms used in this test included gram positive bacteria, gram negative bacteria, yeast and fungi.

Preservative Effectiveness Testing was performed followed the basic USP (United States Pharmacopia) guidelines, with the exceptions being that additional organisms were tested above the specified five USP test organisms and the test frequency varied depending upon the specific type of evaluation. For preliminary evaluations, testing was performed up to seven days, while testing of final formulations was performed for 28 days. In summary, each diluent composition was challenged against a panel of microbial isolates. The initial inoculum concentration was $10^5$–$10^6$ cfu/mL (cfu=colony forming units). The test formulations were maintained at ambient temperature (except test case 12 in which the diluent was stressed at 150° F. for two weeks). At the appropriate test time, diluent aliquots were plated, incubated for a specific time depending on the organism, and colonies counted visually at the specified intervals in Table 5. The results illustrated in Table 5 represent the number of different microorganisms of the initial inoculum present after the period of time exposed to the diluent.

TABLE 5

| Test | 0 Hours | 48 Hours | 72 Hours | 7 Days | 14 Days | 21 Days | 28 Days |
|---|---|---|---|---|---|---|---|
| 1 | 12 | 12 | — | 12 | — | — | — |
| 2 | 12 | 4 | — | 3 | — | — | — |
| 3 | 12 | 4 | — | 2 | — | — | — |
| 4 | 7 | 2 | — | 0 | — | — | — |
| 5 | 12 | 3 | — | 1 | — | — | — |
| 6 | 8 | — | 2 | 0 | — | — | — |
| 7 | 8 | — | 2 | 0 | — | — | — |
| 8 | 12 | 3 | — | 1 | 1 | 0 | 0 |
| 9 | 12 | 3 | — | 2 | 1 | 0 | 0 |
| 10 | 12 | 3 | — | 2 | 1 | 0 | 0 |
| 11 | 12 | — | — | 2 | 1 | 0 | 0 |
| 12* | 12 | — | — | 2 | 1 | 0 | 0 |

*Experimental procedures for Test 12 are identical to Test 11 except for Test 12 the diluent was maintained at 150° F. for two weeks.

This example illustrates that diluent compositions of this invention containing 5-chloro-2-methyl-4-isothiazolin-2-one and 2-methyl-4-isothiazolin-3-one and 5-bromo-5-nitro-1,3-dioxane have sufficient antimicrobial activity for use as multipurpose blood diluents.

Example 4

Comparison of the Effectiveness of ISOTON® Diluent and the Diluent of the Invention in Permitting Measurement of Accurate Physical Parameters of Aged and Fresh Blood Samples The effectiveness of the diluent composition of the instant invention as a multipurpose blood diluent and flow cytometry sheath fluid was compared with that of commercially available Isoton® III diluent. These diluents are comparable in permitting accurate measurement of physical parameters of fresh and aged blood without interference by components of the diluents themselves.

The Test Samples were prepared using aged or fresh blood samples diluted with the diluent of the invention. This diluent was prepared utilizing the components described in Table 1 above. The "Isoton® III" samples were prepared similarly using the same fresh or aged blood samples and with Isoton® III diluent in equivalent amounts and under equivalent conditions to those of the Test Samples.

A number of cytometers were utilized to determine various physical parameters of the fresh and aged blood samples and include the commercially available COULTER® GEN•S, HMx, and STKS hematology analyzers. The abbreviations set forth in Tables 6–11 are defined above. Specifically, Tables 6–8 illustrate the data as obtained from the COULTER® GEN•S instrument; Tables 9 and 10 illustrate the data as obtained from the COULTER® HMx instrument; and Tables 11 and 12 illustrate the data as obtained from the COULTER® STKS instrument.

Once the value of each physical parameter was determined, the differential measurements obtained for the indicated parameters between fresh blood and aged blood samples diluted with Isoton® III diluent and the fresh and aged blood samples diluted with the diluent of the invention were calculated. The results obtained for blood samples diluted with Isoton® III diluent or the diluent of the present invention are reported in the tables below.

TABLE 6

| Samples containing | WBC | RBC | Hgb | Hct | MCV | MCH |
|---|---|---|---|---|---|---|
| Isoton III diluent | | | | | | |
| Fresh | 7.12 | 3.73 | 11.17 | 33.27 | 89.61 | 30.07 |
| Aged | 7.06 | 3.74 | 11.20 | 34.16 | 91.77 | 30.12 |
| Differential | −0.06 | 0.01 | 0.03 | 0.89 | 2.16 | 0.05 |
| Test Diluent | | | | | | |
| Fresh | 7.12 | 3.73 | 11.15 | 33.19 | 89.52 | 30.05 |
| Aged | 7.06 | 3.74 | 11.16 | 34.16 | 91.64 | 29.96 |
| Differential | −0.05 | 0.01 | 0.01 | 0.98 | 2.13 | −0.09 |

TABLE 7

| Samples containing | MCH | MCHC | RDW | Plt | Pct | MPV |
|---|---|---|---|---|---|---|
| Isoton III diluent | | | | | | |
| Fresh | 30.07 | 33.53 | 15.30 | 237 | 0.20 | 8.61 |
| Aged | 30.12 | 32.80 | 16.04 | 237.8 | 0.21 | 8.88 |
| Diff | 0.05 | −0.74 | 0.73 | 0.69 | 0.01 | 0.27 |
| Test Diluent | | | | | | |
| Fresh | 30.05 | 33.56 | 15.34 | 236.7 | 0.21 | 8.65 |
| Aged | 29.96 | 32.67 | 16.04 | 237.4 | 0.21 | 8.93 |
| Diff | −0.09 | −0.89 | 0.70 | 0.71 | 0.01 | 0.28 |

TABLE 8

| Samples containing | PCW | NE % | LY % | MO % | EO % | BA % | RET % | RET # |
|---|---|---|---|---|---|---|---|---|
| Isoton III diluent | | | | | | | | |
| Fresh | 15.95 | 64.19 | 23.09 | 8.83 | 3.28 | 0.61 | 1.63 | 0.06 |
| Aged | 15.95 | 66.55 | 23.48 | 6.07 | 3.42 | 0.49 | 1.42 | 0.05 |
| Diff | 0.00 | 2.36 | 0.40 | −2.76 | 0.13 | −0.13 | −0.20 | −0.01 |
| Test Diluent | | | | | | | | |
| Fresh | 15.82 | 64.28 | 23.01 | 8.89 | 3.24 | 0.58 | 1.79 | 0.07 |
| Aged | 15.88 | 66.25 | 23.66 | 5.85 | 3.53 | 0.71 | 1.41 | 0.05 |
| Diff | 0.06 | 1.97 | 0.65 | −3.04 | 0.29 | 0.13 | −0.38 | −0.01 |

TABLE 9

| Samples containing | WBC | RBC | HGB | MCV | RDW | PLT |
|---|---|---|---|---|---|---|
| Isoton III diluent | | | | | | |
| Fresh | 7.31 | 4.53 | 13.35 | 88.02 | 13.61 | 267.80 |
| Aged | 7.30 | 4.53 | 13.33 | 89.47 | 14.10 | 268.49 |
| Diff | −0.01 | −.01 | −0.02 | 1.45 | 0.49 | 0.69 |
| Test diluent | | | | | | |
| Fresh | 7.32 | 4.54 | 13.28 | 86.83 | 13.67 | 268.26 |
| Aged | 7.22 | 4.53 | 13.26 | 88.74 | 14.33 | 269.58 |
| Diff | −0.11 | −0.01 | −0.02 | 1.91 | 0.65 | 1.31 |

TABLE 10

| Samples containing | MPV | NE % | LY % | MO % | EO % | BA % |
|---|---|---|---|---|---|---|
| Isoton III diluent | | | | | | |
| Fresh | 8.51 | 60.86 | 26.78 | 8.63 | 2.99 | 0.74 |
| Aged | 8.91 | 60.81 | 28.64 | 6.43 | 3.41 | 0.72 |
| Diff | .040 | −0.05 | 1.86 | −2.20 | 0.42 | −0.03 |
| Test diluent | | | | | | |
| Fresh | 8.75 | 60.84 | 26.79 | 8.66 | 2.96 | 0.75 |
| Aged | 9.02 | 59.73 | 29.05 | 6.73 | 3.68 | 0.82 |
| Diff | 0.27 | −1.12 | 2.25 | −1.94 | 0.72 | 0.08 |

TABLE 11

| Samples containing | WBC | RBC | HGB | MCV | RDW | PLT |
|---|---|---|---|---|---|---|
| Isoton III diluent | | | | | | |
| Fresh | 7.95 | 4.44 | 13.43 | 89.52 | 13.65 | 236.33 |
| Aged | 7.86 | 4.45 | 13.44 | 90.64 | 14.36 | 233.60 |
| Diff | −0.09 | 0.01 | 0.00 | 1.12 | 0.71 | −2.72 |
| Test diluent | | | | | | |
| Fresh | 7.93 | 4.44 | 13.37 | 88.74 | 13.75 | 234.94 |
| Aged | 7.82 | 4.45 | 13.39 | 90.55 | 14.58 | 232.39 |
| Diff | −0.11 | 0.00 | 0.02 | 1.81 | 0.84 | −2.55 |

TABLE 12

| Samples containing | MPV | NE % | LY % | MO % | EO % | BA % |
|---|---|---|---|---|---|---|
| Isoton III diluent | | | | | | |
| Fresh | 8.99 | 64.69 | 24.58 | 7.76 | 2.30 | 0.68 |
| Aged | 9.17 | 64.74 | 25.62 | 5.56 | 2.88 | 1.21 |
| Diff | 0.18 | 0.06 | 1.04 | −2.20 | 0.58 | 0.53 |
| Test diluent | | | | | | |
| Fresh | 9.19 | 64.70 | 24.59 | 7.83 | 2.25 | 0.64 |
| Aged | 9.35 | 65.09 | 25.36 | 5.81 | 2.97 | 0.78 |
| Diff | 0.17 | 0.39 | 0.77 | −2.02 | 0.72 | 0.14 |

These data in Tables 6–12 illustrate that the diluent compositions of the instant invention perform similarly to those of commercially available Isoton® III diluent in analytic evaluation of fresh and aged blood samples. Thus, the diluent of the present invention provides the advantages of low formaldehyde production, good anti-microbial activity and at least equivalent efficacy as a multipurpose blood diluent.

In a subsequent experiment, two conventional three-part WBC histograms were generated for aliquots from the same blood sample. One aliquot was diluted with Isoton® III diluent and the second aliquot were diluted with a diluent of the present invention. All other analytic measurements and procedures were identical. The resulting histograms (data not shown) were essentially identical. This experiment also confirms that the diluent of the present invention is as useful as the performance standard Isoton® III diluent in conventional blood sample analyses.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A low formaldehyde containing aqueous blood diluent comprising:

a) an effective potentiator amount of ethylenediamine tetraacetic acid, ethylenediamine tetraacetic acid derivative, or combinations thereof;

b) an effective antimicrobial amount of 5-chloro-2-methyl-4-isothiazolin-3-one and 2-methyl-4-isothiazolin-3-one; and c) an effective antimicrobial amount of 5-bromo-5-nitro-l,3-dioxane;
      wherein said effective amounts of (a), (b) and (c) in combination produce less than about 1 parts per million of formaldehyde in said diluent, and wherein said diluent contains less than 1 parts per million of formaldehyde.

2. The diluent according to claim 1, which does not comprise dimethylolurea.

3. The diluent according to claim 1, further comprising:

d) an alkali metal sulfate;

e) a pH adjuster in an amount sufficient to produce a pH of about 5 to about 8 in said diluent; and f) N-(2-acetoamido)iminodiacetic acid.

4. The diluent according to claim 3, further comprising an alkali metal chloride, wherein said alkali metal chloride and said alkali metal sulfate are present in amounts sufficient to produce an osmolality of about 250 to 350 mOsm and a conductivity of about 16 to about 22.

5. The diluent according to claim 4, where said alkali metal chloride is sodium chloride.

6. The diluent according to claim 3, wherein said alkali metal sulfate is sodium sulfate.

7. The diluent according to claim 3, wherein said pH adjuster is an alkali metal hydroxide.

8. The diluent according to claim 7, wherein said alkali metal hydroxide is sodium hydroxide.

9. The diluent according to claim 1, further comprising ethyl p-aminobenzoate hydrochloride.

10. The diluent according to claim 1, wherein less than about 0.70 parts per million of formaldehyde is produced in said diluent.

11. The diluent according to claim 1, wherein said ethylenediamine tetraacetic acid derivative is disodium ethylenediamine tetraacetic acid.

12. The diluent according to claim 1, wherein said effective amount of said ethylenediamine tetraacetic acid, ethylenediamine tetraacetic acid derivative, or combinations thereof is about 0.05 g/L to about 5.0 g/L.

13. The diluent according to claim 1, wherein said effective amount of said 5-chloro-2-methyl-4-isothiazolin-3-one and 2-methyl-4-isothiazolin-3-one is about 0.0015 g/L to about 0.030 g/L.

14. The diluent according to claim 1, wherein said effective amount of said 5-bromo-5-nitro-1, 3-dioxane is about 0.01 g/L to about 0.5 g/L.

15. The diluent according to claim 1, wherein the pH of said diluent is about 6 to 8.

16. The diluent according to claim 1, wherein the osmolality of said diluent is about 300 mOsm/kg to about 340 mOsm/kg.

17. A method of analyzing a blood sample containing blood cells comprising:
   a) forming a diluted blood sample by mixing a blood sample containing blood cells with said diluent of claim 1; and
   b) analyzing said diluted blood sample to determine a physical parameter of said blood cells.

18. The method according to claim 17, wherein said blood cells comprise red blood cells.

19. The method according to claim 18, wherein said analyzing is performed to determine the mean cell volume of said red blood cells.

20. The method according to claim 17, further comprising mixing a lytic reagent with said diluted blood sample prior to analyzing said diluted blood sample.

21. The method according to claim 20, wherein said lytic reagent comprises an aqueous solution of at least one quaternary ammonium salt.

22. The method according to claim 20, wherein said blood cells comprise white blood cells.

23. The method according to claim 22, wherein said analyzing comprises an automated differential analysis of said white blood cells to determine at least three subpopulations of said white blood cells.

24. The method according to claim 17, wherein said blood cells comprise platelets and said analyzing is performed to determine the number of said platelets in said blood sample.

25. The method according to claim 17, wherein said blood cells contain hemoglobin and said analyzing is performed to determine the hemoglobin content in said blood sample.

* * * * *